(12) United States Patent
Becker et al.

(10) Patent No.: US 7,956,601 B2
(45) Date of Patent: *Jun. 7, 2011

(54) DEVICE AND PROCESS FOR DETECTING PARTICLES IN A FLOWING LIQUID

(75) Inventors: Edwin Becker, Reken (DE); Thomas Knoell, Neu-Ulm (DE); Roland Hoelzl, Munich (DE)

(73) Assignee: Prueftechnik Dieter Busch AG, Ismaning (DE)

( * ) Notice: Subject to any disclaimer, the term of this patent is extended or adjusted under 35 U.S.C. 154(b) by 829 days.

This patent is subject to a terminal disclaimer.

(21) Appl. No.: 11/958,073

(22) Filed: Dec. 17, 2007

(65) Prior Publication Data

US 2009/0051350 A1 Feb. 26, 2009

(30) Foreign Application Priority Data

Aug. 21, 2007 (DE) .......................... 10 2007 039 434

(51) Int. Cl.
G01N 27/74 (2006.01)
G01N 15/06 (2006.01)
G01R 33/12 (2006.01)

(52) U.S. Cl. .......................... 324/204; 73/53.07; 702/149

(58) Field of Classification Search ........................ None
See application file for complete search history.

(56) References Cited

U.S. PATENT DOCUMENTS

| 3,575,050 | A | 4/1971 | Lynnworth |
| 4,380,924 | A | 4/1983 | Nakamoto et al. |
| 4,445,088 | A | 4/1984 | Schübel |
| 4,837,511 | A | 6/1989 | Whittington et al. |
| 5,175,498 | A | 12/1992 | Cueman et al. |
| 5,184,070 | A | 2/1993 | Besendorfer et al. |
| 5,315,243 | A | 5/1994 | Kempster et al. |
| 5,811,664 | A | 9/1998 | Whittington et al. |
| 6,566,871 | B2 * | 5/2003 | Holzl .......................... 324/240 |
| 7,423,424 | B2 * | 9/2008 | Hoelzl et al. ................ 324/240 |
| 7,443,156 | B2 | 10/2008 | Hoelzl et al. |

FOREIGN PATENT DOCUMENTS

| DE | 28 40 358 A1 | 3/1979 |
| DE | 28 50 246 A1 | 5/1980 |
| DE | 39 31 497 A1 | 4/1991 |
| DE | 40 14 756 A1 | 11/1991 |
| EP | 0 451 209 B1 | 8/1994 |
| WO | 2004/081608 A2 | 9/2004 |
| WO | 2004/104561 A1 | 12/2004 |
| WO | 2007/088015 A1 | 8/2007 |

* cited by examiner

*Primary Examiner* — Jay M Patidar
(74) *Attorney, Agent, or Firm* — Roberts Mlotkowski Safran & Cole, P.C.; David S. Safran (57) ABSTRACT

A process and device for detecting electrically conductive particles in a liquid flowing in a pipe section, the liquid being exposed to periodic alternating electromagnetic fields by a transmitter coil which induces eddy currents in the particles, a probe made as a coil arrangement and which has an effective width producing a periodic electrical signal based on the eddy currents. The signal ha a carrier oscillation with an amplitude and/or phase which is modulated by particles passing across the effective width of the coil arrangement, the probe signal being filtered by a frequency-selective first filter unit, the filtered signal being sampled by a triggerable A/D converter stage to obtain a demodulated digital measurement signal, the digital measurement signal being filtered by a digital, frequency-selective adjustable second filter unit to obtain a useful signal, and the useful signal being evaluated to detect passage of electrically conductive particles in the pipe section.

58 Claims, 4 Drawing Sheets

DEVICE AND PROCESS FOR DETECTING PARTICLES IN A FLOWING LIQUID

BACKGROUND OF THE INVENTION

1. Field of Invention

The invention relates to a process and a device for detecting electrically conductive particles in a liquid flowing through a pipe by means of eddy currents.

2. Description of Related Art

German Patent Application DE 2 108 717 A1 describes a process and device of the type to which the present invention is directed, two induction coils being located in two branches of an alternating current bridge circuit, the other two branches of which are formed by the halves of another coil. Liquid flows through the coils in the axial direction and the coils can be arranged in succession in the flow direction, the impedance changes which are caused by the passage of the particles and the difference of the impedance change in both coils being evaluated. An arrangement is shown in which the liquid flow is divided into two parallel component sections which each flow through one of the two coils, then an axial offset of the coils is not necessary.

A similar device is described in German Patent Application DE 28 40 358 A1.

The company momac GmbH & Co. KG, 47408 Moers, Germany sells a device under the name "metalscan" in which three coils are arranged in succession in the flow direction, the first and the last coil acting as the transmitter coils and the middle coil acting as the receiver coil to detect passage of electrically conductive particles from a lubricant circuit. The first and the last coil are polarized in reverse.

Other devices in which the signal from the induction coils through which a liquid has flowed is used for particle detection are described for example, in International Patent Application Publications WO 2004/081608 and WO 2004/104561, and European Patent Applications EP 0 778 937 A2 and EP 0 451 209 B1.

German Patent Application DE 39 31 497 A1 discloses a process for inductive detection of particles in lubricants, a coupling coil embedded in a coil through which flow takes place axially being resonantly excited and the passage of particles being detected using the energy removed from the coil system by the eddy currents. In this connection the particle size is determined from the signal amplitude. In order to prevent adulteration of the measurement by the coil sensitivity which decreases in particle passage in the coil middle compared to the coil edge, a swirl generator provides for the particles passing the coil always near the coil wall.

German Patent Application DE 31 17 319 A1 describes detection of the flow velocity of a liquid metal by means of eddy current measurement using a cross correlation function.

German Patent Application DE 40 14 756 A1 describes determination of the velocity of a body or material by means of eddy current measurement, a correlation function being performed.

U.S. Pat. No. 3,575,050 and German Patent Application DE 28 50 246 A1 mention that there are flowmeters based on eddy currents.

A conventional measurement process for nondestructive and noncontact detection of faults in a test specimen, especially a semi-finished metallic article, is induction and measurement of eddy currents in the test specimen. In this connection, the specimen is exposed to periodic alternating electromagnetic fields by means of a sinusoidally energized transmitter coil. The eddy currents induced thereby in the specimen in turn in the coil arrangement which is used as a probe and which can have a single coil ("absolute coil") or two subtractively connected coils ("difference coil") induce a periodic electrical signal which has a carrier oscillation according to the transmitter carrier frequency with an amplitude and/or phase which is modulated by the fault in the specimen in a characteristic manner when the fault travels into the sensitive region of the probe, i.e., into the effective width of the probe. The transmitter coil forms the primary side and the receiver coil(s) form the secondary side of a transformer arrangement. One example of this arrangement can be found in European Patent Application EP 1 189 058 A2. If more than two receiver coils are used, this arrangement is also called a "multi-difference coil".

Conventionally, to scan the specimen the latter is moved linearly with respect to the probe, but also arrangements with a rotating probe being known. The signal detected by the probe is conventionally demodulated in analog fashion, for example, by means of synchronous demodulation, and then, is subjected to evaluation in order to detect faults in the specimen. The signal is digitized conventionally first for evaluation and display of the fault signal, i.e., after demodulation of the coil signal. One example of this process can be found in German Patent Application DE 40 03 330 A1.

Similarly, electrically conductive particles in a liquid which is flowing through the coils cause eddy current losses which in turn are reflected in a measurable impedance change of the coils. In this way, by means of an inductive coil arrangement, electrically conductive particles in a liquid flowing in a pipe can be detected. This is especially advantageous when the concentration of metallic particles in the lubricant circuit of a machine is to be detected in order to draw conclusions about the machine state (the concentration of metallic particles is generally a measure of machine wear).

These eddy current measurement processes are relatively complex and expensive due to the effort required for analog demodulation. Furthermore, it must be considered that ordinarily different filter sets for the demodulated signal are necessary for different relative velocities of the specimen to the probe, i.e., for different ejection or test speeds; this entails additional cost when the specimen velocity is variable.

U.S. Pat. No. 5,175,498 describes an eddy current measurement process in which the measurement signal received by the coil probe is digitized by means of a triggerable A/D converter, and then, in digital form, is demodulated by means of a Fourier transform. Triggering of the A/D converter, i.e., the sampling rate, is controlled depending on the forward velocity of the specimen which has been detected by means of an encoder, in order to avoid errors resulting from backward motion of the specimen in the signal evaluation.

U.S. Pat. No. 4,445,088 describes a magnetic stray flux measurement process in which a metallic specimen is moved relative to a probe, the measurement signal which has been detected by the probe being digitized after passing through a bandpass filter by means of a triggerable A/D converter, the triggering of the converter, i.e., the sampling rate, being controlled by the advance rate of the specimen which is detected by means of a velocity sensor. For fault detection, the amplitude of the digitized signal is evaluated with respect to a threshold value being exceeded, the choice of the sampling rate depending on the test speed being used to achieve a given measurement accuracy which is independent of the specimen velocity.

International Patent Application Publication WO 2006/007826 A1 describes an eddy current measurement process for detecting faults in a specimen moved relative to a probe which is characterized by an effective width with a velocity, by means of the probe a periodic electrical signal being detected which has a carrier oscillation with an amplitude and/or phase which is modulated by a fault in the specimen, the probe signal being filtered and being sampled by means of a triggerable A/D converter stage in order to obtain a demodulated digital measurement signal which is filtered by means of a digital, frequency-selective, adjustable second filter unit in order to obtain a useful signal which is evaluated to detect a fault in the specimen, the A/D converter stage being triggered with a n-th, integral fraction of the frequency of the carrier oscillation, n being chosen as a function of the fault frequency which arises as the quotient of the relative velocity between the specimen and probe and the effective width of the probe, and the frequency-selective second filter unit being set as a function of the fault frequency.

SUMMARY OF THE INVENTION

A primary object of this invention is to devise an especially simple process for detecting electrically conductive particles in a liquid flowing in a pipe section. Furthermore, a related object is to provide a device suitable for executing such a process.

This object is achieved in accordance with the invention by a process and device as described herein.

One important aspect of this invention is that the probe signal is sampled with an integral fraction of the frequency of the carrier oscillation, i.e., is digitized, i.e., undersampling of the carrier oscillation takes place. In this way, the carrier oscillation is eliminated from the measurement signal, by which the otherwise conventional demodulation of the measurement signal is eliminated and thus a major simplification of the process and a major reduction of the cost for the otherwise necessary demodulation, for example, analog synchronous demodulation, can be achieved; this leads to major cost savings, and optionally, also to saving of installation space.

Furthermore, the undersampling enables use of A/D converters with very high resolution which are usually relatively slow, i.e., relatively limited in their maximum sampling rate.

Moreover, the undersampling leads to the useful signal being obtained with a relatively low data rate; in turn, this facilitates the display of the useful signal so that, for example, standard bus systems and possibly wireless bus systems can be used; this would not be possible at high data rates or would only be possible after data compression.

In addition, the undersampling allows the measurement process to be carried out with relatively low power consumption, even during time intervals in which sampling does not take place, the transmitter could be turned off if, for example, sampling is done only for each tenth period of the carrier oscillation or even less often. This aspect is especially important for portable devices in battery operation or if a cableless probe, i.e., one connected wirelessly to the evaluation unit, is to be used.

Finally, in undersampling, as compared to quasi-continuous sampling, a reduction in the susceptibility to nonperiodic noise signals can arise, since these noise signals, if they do not fall into the respective sampling interval, are not perceived at all in the useful signal, while in quasi-continuous sampling all noise signals are reflected in the useful signal.

Preferably, the transmitter coil surrounds the pipe section, the coil arrangement having at least one first inductive receiver coil surrounding the pipe section and a second inductive receiver coil which is spaced axially to the first receiver coil and which surrounds the pipe section, which receiver coils are located in the region of the transmitter coil and are subtractively connected in order to output a difference signal according to the eddy currents induced by the transmitter coil, the transmitter coil forming the primary side and the receiver coils forming the secondary side of a transformer arrangement, and the probe signal being formed from the difference signal. In this way all coils are located near one another and thus are exposed to essentially the same environmental influences, for example, with respect to temperature; this increases measurement accuracy.

According to another important aspect of the invention, the sampling rate, i.e., the degree of undersampling, is selected as a function of the particle frequency which is defined as the quotient of the flow velocity of the liquid and the effective width of the probe.

Since the duration of the useful signal caused by a particle in the liquid, and thus, the particle frequency, depend essentially only on the extension of the sensitive region of the probe, i.e., the effective width, and the flow velocity of the liquid, it can be ensured in this way, on the one hand, that the accuracy of display of the useful signal does not depend on the flow velocity (by the corresponding choice of the sampling rate, it can be ensured that roughly the same number of sampling points always end up in each particle signal), and on the other hand, it can be ensured that the signal of a particle appears essentially the same regardless of the flow velocity; this facilitates recognition of particle passage.

Another advantage of undersampling matched to the flow velocity is that, in this way, the digital filter unit, by means of which the digital signal delivered by the A/D converter stage is filtered in order to obtain a useful signal free of noise, can be set very easily depending on the particle frequency, specifically by clocking the digital filter with the sampling rate (in a digital filter, the corner frequency depends directly on the clock-pulse rate). In this way, a single filter set can be used and it is automatically matched to the bandwidth of the particle signal which is dependent on the flow velocity with its corner frequencies by the corresponding choice of the sampling rate, i.e., clock-pulse rate.

The particle frequency ordinarily corresponds to the peak of the particle spectrum, i.e., to the frequency with the highest intensity. The bandwidth of the particle signal is the frequency range around the particle frequency in which information critical for particle recognition can be found. The effective width of the probe depends on the one hand on the geometrical configuration of the probe, but also on the outline conditions of use of the probe. Physically the effective width corresponds to the length which corresponds to the reciprocal particle frequency and results from the flow velocity divided by twice the particle frequency. The effective width thus indicates the length over which a particle can influence the measurement signal received by the probe.

The alternating current voltage for the transmitter coil can be produced from a binary signal by waveforming, preferably the trigger signal for the A/D converter stage being produced by the frequency of the binary signal used for producing the transmitter alternating current voltage being divided by a whole number. The whole number by which the frequency of the carrier oscillation is divided to trigger the A/D converter stage is chosen to be preferably inversely proportional to the particle frequency, so that the selected sampling rate can be chosen to be at least roughly proportional to the particle frequency. Preferably this whole number is chosen such that at least 5, preferably at least 20, but at most 100, preferably at most 50, samplings by the A/D converter stage fall into the base interval, i.e., a time interval which corresponds to the inverse of the particle frequency.

As already mentioned, the frequency-selective second filter unit can be automatically set depending on the particle frequency by the second filter unit being clocked with the sampling rate per A/D converter stage since the corner frequency in a digital filter is directly proportional to the clock frequency. Advantageously, the second filter unit has a low-pass filter in order to mask the portions above the particle bandwidth, and a high-pass filter to mask the uniform portions of the digital signal. Advantageously, the corner frequency of the low-pass filter is above the particle frequency, preferably above twice the particle frequency, while the corner frequency of the high-pass filter is below the particle frequency, preferably below a quarter of the particle frequency. Since the preferred corner frequencies of the second filter unit depend directly on the base frequency, because the scanning rate of the signal is likewise chosen depending on the particle frequency and the second filter unit is clocked with this sampling rate, automatic optimum matching of the corner frequencies of the filter unit to the particle frequency, i.e., the flow velocity and effective width of the probe, can be easily achieved. Fundamentally, the corner frequencies can be nearer to the particle frequency than in conventional processes, since the indicated tracking of the filter with respect to the particle frequency, i.e., especially the flow velocity, reduces the danger that the filters cuts off information which is useful for detecting particle passage.

Preferably, the frequency of the carrier oscillation is chosen such that it is at least ten times, still better at least twenty times, the particle frequency, since otherwise the reproducibility of particle detection (i.e., the reproducibility of the signal which is typical for particle passage) can be adversely affected; this would make particle detection more difficult.

Although fundamentally approaches are also possible in which only a single value per sampled full wave is detected, then the phase angle would have to be indirectly determined, preferably two values with a fixed phase offset being obtained per sampled full wave, this being done preferably with two A/D converters, i.e., the converter stage has two A/D converters which are connected in parallel and which are triggered with the same frequency such that they sample offset by a fixed phase difference, the phase difference preferably being 90° or an integral multiple of 360° plus 90° (however, the phase difference need not absolutely be exactly 90°, but could be, for example, between 85° and 95°). By means of this phase-offset sampling, it can be ensured that, in spite of undersampling, the maximum signal information is obtained, and the digital measurement signal is obtained as a two-component signal, i.e., with phase information and amplitude information, by which particle detection is improved. In this connection, it is advantageous that the two components of the digital measurement signal delivered by the A/D converter stage which is equipped with two A/D converters are filtered separately by means of the second filter unit in order to obtain the useful signal as a two-component signal, and then, the two components can be considered in the evaluation of the useful signal.

In order to execute this phase-offset sampling, it is not necessarily required that exactly two A/D converters be used. Instead, only a single, relatively high-speed A/D converter could be used which undertakes both samplings, for example, that at 0° and that at 90°, these two sampled values then being further processed separately as when using two A/D converters in order to achieve a two-component signal evaluation. Use of very slow A/D converters would be possible when, for example, 4, 8, or 16, etc. A/D converters are used which then do not become active for each trigger pulse to the A/D converter stage, but only for every 2nd, 4th or 8th, etc., i.e., the sampling work for each of the two phase angles is divided accordingly in time among several A/D converters at a time.

Preferably, the A/D converter stage has a resolution of at least 16 bits, preferably, flash converters or SAR converters being used.

Fundamentally, the transmitter coil acting on the liquid, i.e., incident irradiation of alternating electromagnetic fields, can be interrupted at least for part of each interval between two successive trigger signals for the A/D converter stage since, in this time, there is no signal detection, i.e., sampling, anyway (depending on the individual case these sampling pauses can extend under certain circumstances over many periods of the carrier oscillation). In this way, especially for portable measurement devices, a major saving of energy consumption can be achieved, by which, for example, the power supply elements can be greatly reduced in weight and dimensions. Similarly, on the signal detection side the electronics, i.e., especially the signal processor, can be shut down to save energy during the interval between two samplings.

The first filter unit preferably has a low-pass filter which acts as an aliasing filter with respect to sampling by the A/D converter stage. Furthermore, preferably a high-pass filter is provided in order to mask low frequency noise signals. The first filter unit will conventionally be made as an analog filter. Also, downstream of the first filter unit, there is a controllable amplifier in order to bring the filter signal to the amplitude which is optimally suited for the A/D converter stage.

The control of the A/D converter stage, i.e., the choice of trigger instants, and the processing of the digital signal delivered by the A/D converter stage, takes place preferably by means of a digital signal processor which preferably also forms the second filter unit. The trigger means for triggering the A/D converter stage preferably has a source for a binary signal which can be formed by a timer, and a divider which divides the binary signal by a whole number in order to produce the trigger signal for the A/D converter stage, the binary signal being processed by a waveformer in order to deliver the supply voltage for the transmitter. The timer can be made as part of the digital signal processor or separately from it. The divider is preferably made separately from the signal processor as a PAL (Programmable Array Logic) module.

Fundamentally, the flow velocity of the liquid can be determined by measurement. Typically, the pipe section is part of a lubricant circuit, the liquid being the lubricant of a machine. In these cases, the liquid flow rate is usually known and is essentially constant, so that it is not necessary to measure the flow velocity of the liquid and the velocity can be fixed as a parameter for signal detection and evaluation.

The invention is explained in detail below with reference to the accompanying drawings.

DETAILED DESCRIPTION OF THE INVENTION

Figure 3:
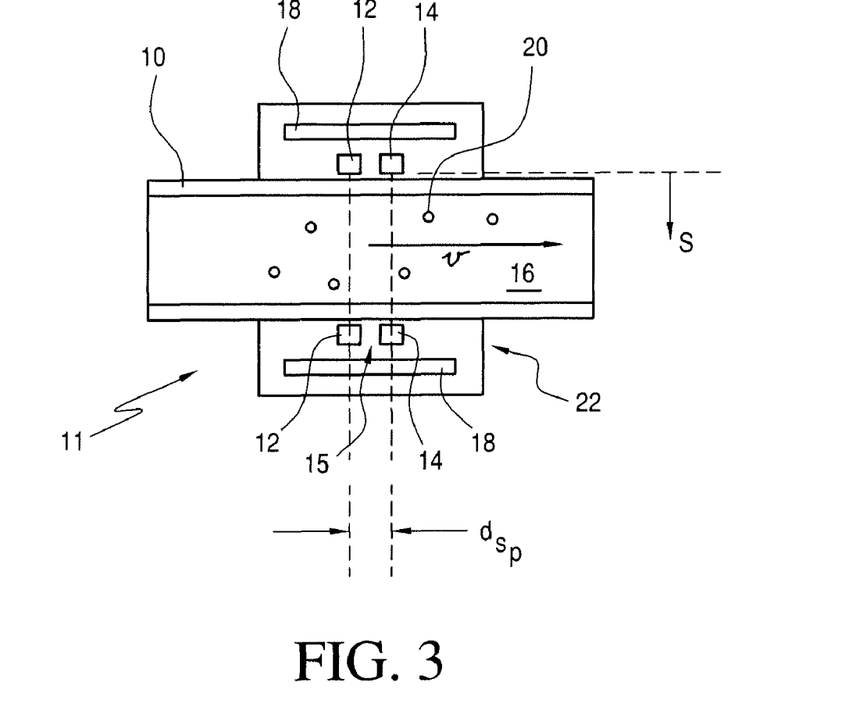
FIG. 3 is a lengthwise section of a pipe through which a liquid is flowing and which is provided with transmitter and probe coils for use with the measurement device of FIG. 1.

As shown in FIG. 3, a pipe section 10 is surrounded by a first inductive receiver coil 12 and a second inductive receiver coil 14 located spaced apart from it in the axial direction so that a liquid 16 which is flowing in the pipe section 10 flows through the coils 12 and 14 in the axial direction. The axial distance of the two coils 12, 14 and the axial dimension of the coils 12, 14 can be for example, 2 mm. The two receiver coils 12, 14 are surrounded externally by a transmitter coil 18 which is located coaxially to the two coils 12, 14 and which has a greater diameter than the latter. The axial dimension of the transmitter coil 18 is such that the two receiver coils 12, 14 are located entirely within the transmitter coil 18. Preferably, the extension of the transmitter coil 18 in the axial direction is at least twice as great as the axial extension of the arrangement of the receiver coils 12, 14, i.e., distance plus axial extension of the coils 12, 14. The coils 12, 14, 18 are located in a housing 22 which surrounds the pipe section 10 and they form a measurement head 11.

Typically the pipe section 10 is part of a lubricant circuit of a machine, the liquid 16 then being a lubricant in which there are metallic particles which are typically wear debris from the moving parts of the machine. A typical value for the lubricant flow rate in the main flow is 10 liters/min. At much higher flow rates it is a good idea to measure, not in the main flow, but in a secondary flow.

Figure 4:
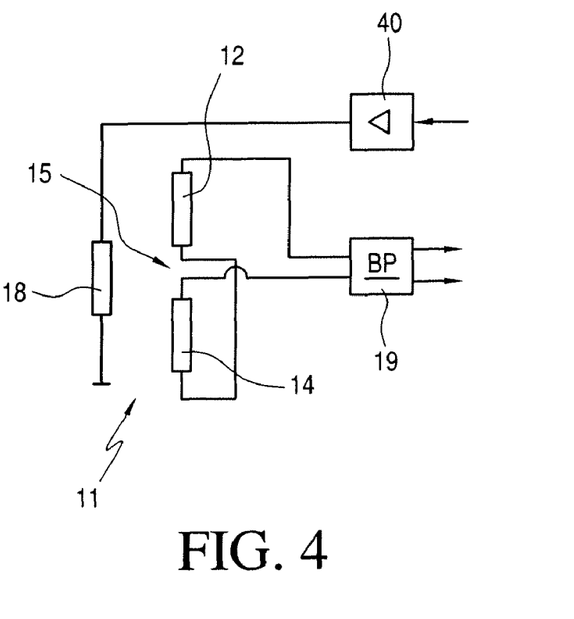
FIG. 4 is a circuit diagram of the interconnection of the coils of FIG. 3.

As shown in FIG. 4, the two receiver coils 12, 14 are connected subtractively as a difference coil 15, i.e., are arranged oppositely so that in both coils 12, 14 a voltage with the same absolute value but opposite sign is induced. Altogether the transmitter coil 18 and the receiver coils 12, 14 form a transformer arrangement, the transmitter coil 18 forming the primary side and the receiver coils 12, 14 forming the secondary side. The transformer core in this arrangement is formed by the materials or media penetrating the coils 12, 14, 18, i.e., air, the housing 22, the pipe 10, and the liquid 16 with the particles 20.

The impedance difference of the coils 12, 14 which is caused by the particles 20, i.e., the difference of the impedance of the two coils 12, 14 caused by the instantaneous presence of a particle 20 in one of the two coils 12, 14 (the particles 20 are much smaller than the distance of the coils 12, 14) is represented by the measurement signal which has been output from the coils 12 and 14.

A device for detecting electrically conductive particles in a liquid flowing through a pipe by means of eddy currents as described above forms the subject matter of the present inventor's, commonly owned, co-pending U.S. patent application Ser. No. 11/958,001 to which reference is made for further details of this aspect of the device of the present invention.

Figure 1:
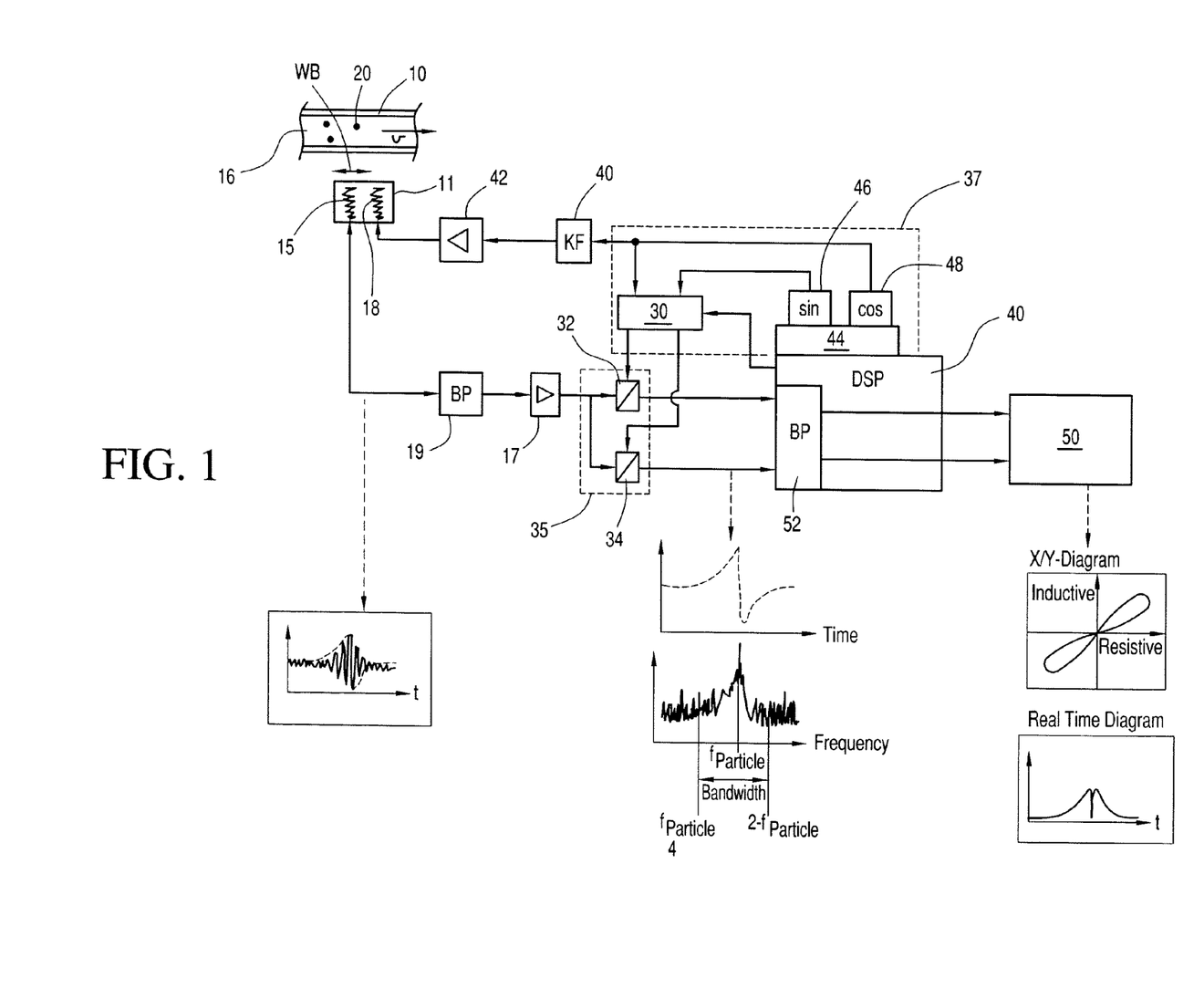
FIG. 1 schematically shows the structure of one embodiment of an eddy current measurement device for detecting conductive particles in a liquid in accordance with this invention.

FIG. 1 shows an example of the structure of an eddy current measurement device in accordance with the invention which uses a measurement head 11.

The transmitter coil 18 is used to induce eddy currents in the particles 20 by means of an alternating electromagnetic field with at least one given carrier frequency; these eddy currents in the receiver coil 15 which is made as a difference coil in turn induce an alternating current voltage which acts as the probe signal and which has a carrier oscillation with the carrier frequency of the transmitter coil 18, the amplitude and the phase of the probe signal being modulated by a particle 20 when the latter ends up in the effective width WB of the receiver coil 15.

The voltage for the transmitter coil 18 can be produced for example, by a binary signal which has been generated by a timer unit 44 being delivered to a generator 48 as a specified frequency which produces therefrom a rectangular signal or also a sinusoidal signal which passes through a waveformer 40 and then is amplified by means of a power amplifier 42 before it is supplied to the transmitter coil 18. Preferably the signal has a sinusoidal shape and in the simplest case contains only a single carrier frequency, however fundamentally measurements with simultaneously several carrier frequencies and/or carrier signals clearly deviating from sinusoidal oscillations also being possible. Preferably, the carrier frequency is in the range from 20 kHz to 500 kHz.

The probe signal received by the receiver coil 15 passes through a bandpass filter 19 and an adjustable preamplifier 17 before it is supplied to the A/D converter stage 35. The bandpass filter 19 is used, on the one hand, by means of the low-pass filter as an (anti-)aliasing filter with respect to digitization of the signal by the A/D converter stage 35, and on the other hand, by means of the high-pass filter to mask low-frequency noise signals. The adjustable preamplifier 17 is used to bring the amplitude of the analog probe signal to the amplitude which is optimally suited for the A/D converter stage 35.

The A/D converter stage 35 has two A/D converters 32, 34 which are connected in parallel and which should have high resolution, but at least resolution of 16 bits, preferably at least 22 bits, and should be able to carry out preferably at least 500 A/D conversions per second. The A/D converters 32, 34 are preferably made as flash converters or SAR (successive approximation register) converters.

The A/D converter stage 35 is triggered by a trigger means 37 which has the already mentioned timer unit 44, a cosine generator 48, a sine-wave generator 46 located parallel thereto, and a frequency divider 30. On the input side, on the frequency divider 30 is the signal which is generated by the cosine generator 48 and which has the frequency of the carrier frequency of the supply signal of the transmitter coil 18, and the signal of the sine-wave generator 46 which corresponds to the signal of the cosine generator 48, but is phase-shifted by 90° to it. In the frequency divider 30, these two signals are divided with respect to their frequency by a whole number n. The corresponding frequency-reduced output signal is used to trigger the A/D converter 32 or the A/D converter 34. The choice of the number n for the divider 30 is made by a digital signal processor 40 depending on the "particle frequency" which is the quotient of the flow velocity v of the liquid 16, i.e., the velocity of the particles 20, and the effective width WB of the receiver coil 15. Preferably, n is chosen to be inversely proportional to the particle frequency in order for the trigger rate of the A/D converter stage 35 to be at least roughly proportional to the particle frequency. This results in that, when the effective width WB in the first approximation is assumed to be constant, at a higher flow/particle velocity v, and thus, higher particle frequency, the analog probe signal is sampled accordingly more often.

Preferably, the divider 30 is made as a so-called PAL (programmable array logic) module in order to ensure that the trigger signals arrive with as little delay as possible, i.e., synchronously, with respect to the output signal of the cosine generator 48 and sine-wave generator 46 and without phase jitter at the A/D converter stage 35.

Due to the corresponding phase shift of the two input signals of the divider 30, triggering of the two A/D converters 32, 34 also takes place with a fixed phase offset of 90°. In this way, the analog probe signal can be evaluated in a two-component manner, i.e., both with respect to amplitude and also phase. It goes without saying that the phase delay between the trigger signal of the A/D converter stage 35 and the signal of the transmitter coil 18 should be as low as possible, especially also so-called phase jitter should be avoided, i.e., the phase relations should be as exactly constant as possible in time.

Figure 2:
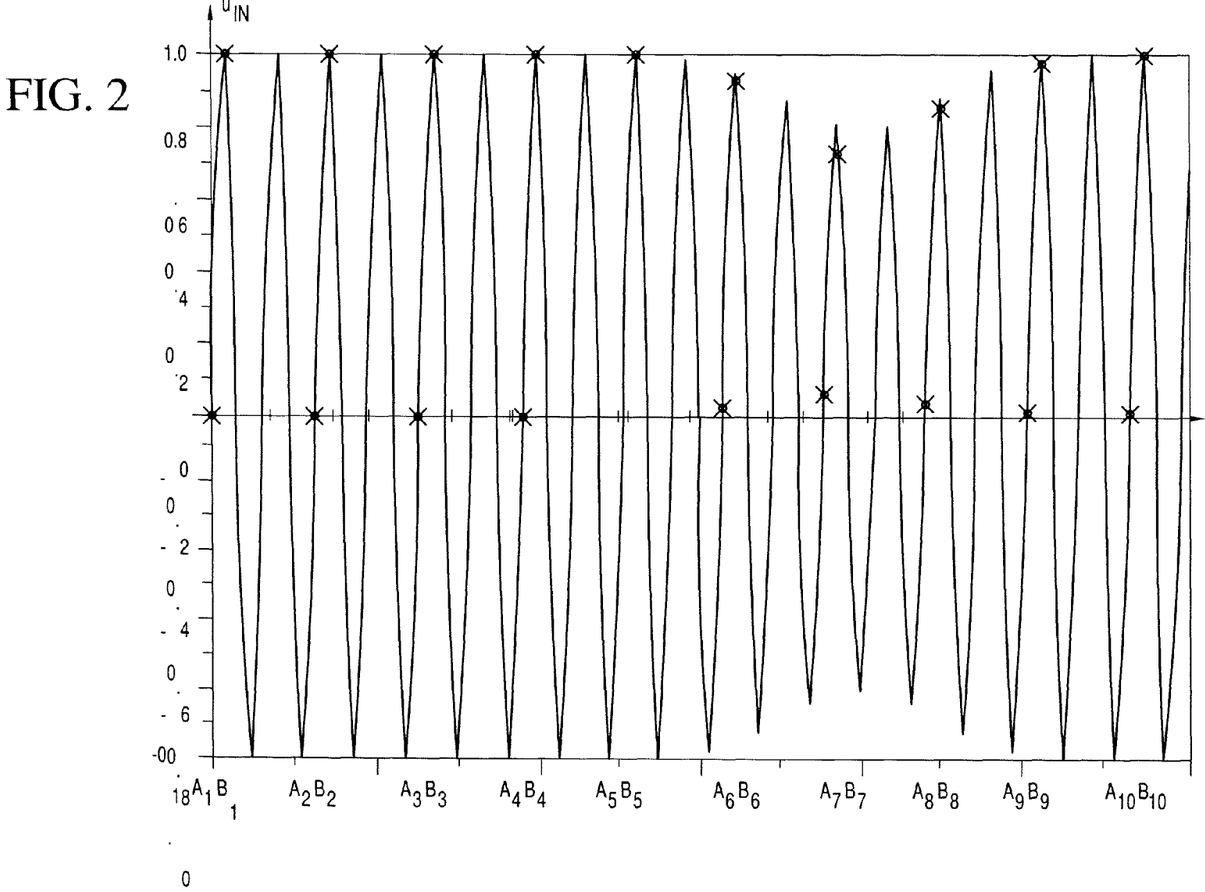
FIG. 2 is a graph showing a sample characteristic of the probe signal during digital sampling.

With the illustrated trigger means 37, it is ensured that the analog probe signal from each A/D converter 32, 34 is sampled at most once per full wave of the carrier oscillation (in this case, n is equal to 1). However, depending on the particle frequency at the time, i.e., the particle velocity v, n can become much larger than 1, so that only one sampling at all takes place in each n-th full wave of the carrier oscillation. FIG. 2 shows an example in which n is equal to 2, i.e., sampling $A_n$ and $B_n$ is performed only in every other full wave by each A/D converter 32, 34 respectively.

However, in all cases, since sampling is performed at most once per full wave per A/D converter 32, 34, the frequency of the carrier oscillation, i.e., the carrier frequency, is eliminated from the digital signal by this undersampling, i.e., demodulation of the analog probe signal takes place by means of undersampling.

Preferably, n is chosen such that, in the time interval in which a noticeable particle signal is observed, i.e., in the time interval in which one point of a particle 20 moves through the effective width WB of the receiver coil 15, i.e., in the time interval which corresponds essentially to the inverse of the particle frequency, at least 5, preferably at least 20 samplings by each A/D converter 32, 34 are undertaken, in order to obtain the information contained in the particle signal still in a manner which is adequate for reliable particle recognition. However, generally, not more than 50, at most 100 samplings will be necessary during such a time interval.

The frequency of the carrier oscillation should be chosen such that it is at least ten times the particle frequency since otherwise the particle signal is carried by too few full waves of the carrier oscillation and the reproducibility of particle detection becomes a problem.

The demodulated, digital, two-channel output signal of the A/D-converter stage 35 passes through a digital bandpass filter 52 which can be represented by the signal processor 40 and which can be used to mask the noise signals which are outside of the bandwidth of the particle signal. For this purpose, the corner frequency of the high-pass filter is preferably chosen such that it is less than one fourth of the particle frequency, while the corner frequency of the low-pass filter is preferably chosen such that it is at least twice the particle frequency in order to avoid masking of signal portions which still contain information with respect to particle passage.

The digital bandpass filter 52 is clocked with the sampling rate of the A/D converter stage 35, i.e., the trigger rate; this entails the major advantage that the corner frequencies of the bandpass filter when the particle frequency changes, i.e., when the particle velocity v changes, are automatically entrained with the particle frequency since the corner frequencies of a digital bandpass filter are proportional to the clock pulse rate, and the clock pulse rate is automatically matched to the change of the particle frequency via the sampling rate which is automatically dictated by the trigger unit 37.

The information required for determining the particle frequency with respect to the effective width WB can be input to the signal processor 40 either manually or it is made available directly from the measurement head 11, as is described for example, in European Patent Application EP 0 734 522 B1.

It goes without saying that the measurement system reacts analogously to the change of particle frequency which is caused by the particle velocity v being kept constant, but by the receiver coil 15 being replaced by another with a different effective width WB.

In particular, at relatively large values of n, i.e., when only a relatively small number of full waves of the carrier oscillation is sampled at all, during the sampling pauses for example, the transmitter coil 18 and/or the evaluation electronics, i.e., especially the signal processor 40, can be turned off or powered down in order to reduce the power consumption; this is especially important for portable measurement devices.

The useful signal obtained after filtering by the digital bandpass filter 52 is evaluated in an evaluation unit 50 in order to detect the passage of particles 20, here conventionally both the amplitude information and also phase information of the particle signal being used.

Advantageously, the evaluation unit 50 is made such that counting of the detectable particle passages takes place in order to be able to draw conclusions regarding the particle concentration in the liquid 16, and thus, optionally regarding the machine state.

Fundamentally, in a difference coil as a result of difference forming (the individual coils of the difference coil are not exactly the same in practice) the so-called coil offset voltage is formed which can exceed the actual difference signal, for example, by two to three orders of magnitude. The resulting relatively high amplitude of the receiver coil signal compared to the actual useful signal imposes high demands on the A/D converter, especially on its resolution.

If the A/D converters which are available at an acceptable price for the receiver coil signal do not meet these requirements, it is possible to compensate for the coil offset voltage with a D/A converter before it is supplied to the A/D converter. In this connection, upstream of the A/D conversion, the receiver coil signal is subjected to an offset which has been determined beforehand in averaging with low gain from the (demodulated) receiver coil signal (in a complex representation of the receiver coil signal by means of compensation of the coil offset voltage by exposure to a suitable offset by means of the D/A converter, the useful signal is moved into or near the origin of the complex plane; the remainder of the coil offset voltage an be eliminated in the processing of the output signal of the A/D converter). During the measurement, this offset value can be further corrected if the averaging is allowed to continue at high gain.

As shown in FIG. 2, the signal for the transmitter coil 18 is produced with a waveformer 40. However, if for reasons of power, a class of D-amplifiers is to be used, it is more advantageous to directly mask the pulse duration modulation (PDM) signal via a sequential digital memory. The transmission frequency is then controlled exclusively via the frequency of the output rate. When the coil 18 is triggered with a suitable PDM signal, it emits a sinusoidal field. This has the advantage that no harmonics are emitted and the sensitivity of the measurement device is concentrated more strongly on the transmission frequency, so that the measurement device is improved in its quality.

Instead of using a "normal difference coil" as shown in FIGS. 3 & 4 which comprises two subtractively connected coils, a multi-difference coil can also be used which then has for example, four receiver coils, each of the two receiver coils 12 and 14 of the normal difference coil being replaced by two receiver coils connected back to back. A multi-difference coil has better noise suppression, i.e., a better signal-to-noise ratio, than a normal difference coil, and the signal form is more pronounced. In any case, the structure is more complex and the signal amplitudes are smaller. Possibly disruptive pre- and post-oscillations are also obtained.

The signal generated by the difference coil when a particle passes through will be called the "difference signal" below.

The size of the detected particles is typically between 1 and 25 μm. Larger particles are conventionally filtered out of the lubricant to prevent damage to the machine.

Advantageously, the number of detected particles per unit of time is determined, from which the concentration of electrically conductive particles in the liquid can be determined, since the liquid flow rate is usually known and is essentially constant.

Not only can passage of a particle be detected from the evaluation of the difference signal of the receiver coils, but also additional information can be obtained, especially with respect to the radial position of the particle in passage through the receiver coils, i.e., the radial distance of the particle from the wall of the receiver coils, the flow velocity of the detected particle, the size of the detected particle and of the volumetric flow, i.e., the flow velocity of the liquid 16 averaged over the cross section of the pipe section 10. How such additional information can be obtained will be explained below using FIGS. 5 to 8 by way of example.

Generally, for a particle counter, it is also desired to detect the volumetric flow in order to be able to normalize the counted particles to a volume (particle/ml) and to assign them to existing standard tables. In this connection, at a given pipe diameter, the velocity of the liquid must be measured, from which then the volume of the lubricant which has passed the particle counter during the measurement time (typically 1 to 30 minutes) can be computed. While there are fundamentally many different—more or less complex—approaches, based on temperature measurement, ultrasound, pulses from mechanical mill wheels, etc., it is especially advantageous to derive the volumetric flow from the eddy current signals which are detected anyway for particle counting. In this way, a design without additional sensors can be implemented; this leads to lower costs, lower failure probability and a smaller space requirement. In this case, the flow velocity can only be detected when particles are recognized. However, generally, this is not a problem, since the measurement only takes place anyway when particles are also being recognized.

Furthermore, it is advantageous for a particle counter to estimate the size of the detected particles and to classify the detected particles according to the estimated size in order to achieve a characterization of the machine state as definitive as possible. For example, when a given boundary value for the number of particles detected overall or for a certain size class per unit of time is exceeded, an alarm signal can be output.

Since both the amplitude and also the time behavior of the difference signal caused by a particle depends on the radial position of the particle in the pipe section 10 or in the coil, it is advantageous both for velocity measurement and volumetric flow measurement as well as for particle size measurement to estimate the radial position of the particle and to correct the velocity measurement or size measurement accordingly.

Figure 5:
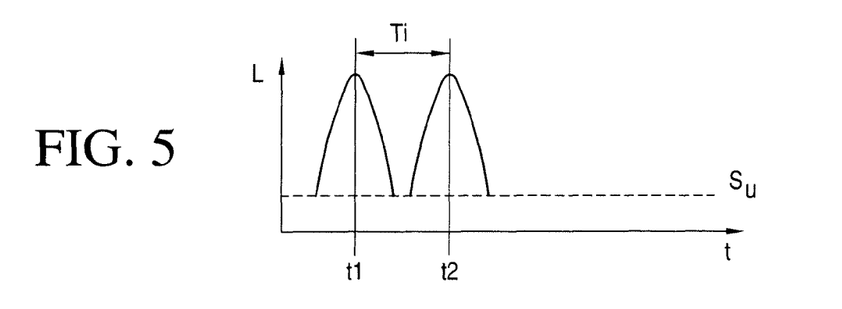
FIG. 5 is a graph showing the idealized behavior of the absolute value of the signal of the receiver coils from FIG. 3, the measured values having been cut off below a threshold value.

FIG. 5 shows an example for the idealized behavior of the absolute value of the difference signal of a normal difference coil, such as, for example, the difference coil formed from the receiver coils 12, 14 of FIG. 3, the measured values having been cut off below the amplitude threshold value $S_u$ (the signal which has been cut off comprises base noise and the start and end of the difference signal). As long as the signal amplitude is above the threshold value $S_u$, the signal is recorded and stored in the processor of the evaluation unit. Two separate signal curves are obtained which each have a peak at time $t_1$ and $t_2$.

The respective amplitude peak, i.e., the respective instant $t_1$ and $t_2$, can be determined for example, by a parabolic balancing computation or more simply by a maximum value search. For subsequent evaluation, what is decisive is the value of the amplitude peak $A_i$ and the time difference $T_i$ which follows from the difference between $t_1$ and $t_2$. For each counter event, i.e., for each found particle i, the corresponding maximum amplitude $A_i$ of the difference signal (optionally also complex) and the pertinent time difference $T_i$ are stored.

Since the two difference coils 12, 14 have a spacing $d_{Sp}$ in the axial direction, the time difference $T_i$ in a first approximation is proportional to the flow velocity $v_i$ of the particle. The axial distance of the coils is reflected in the so-called effective width WB of the difference coil. Fundamentally, the relationship $v_i = k*WB/T_i$ applies. The factor k depends on certain properties of the difference coil and can be determined at the factory one time for the respective type of particle counter.

Figure 7:
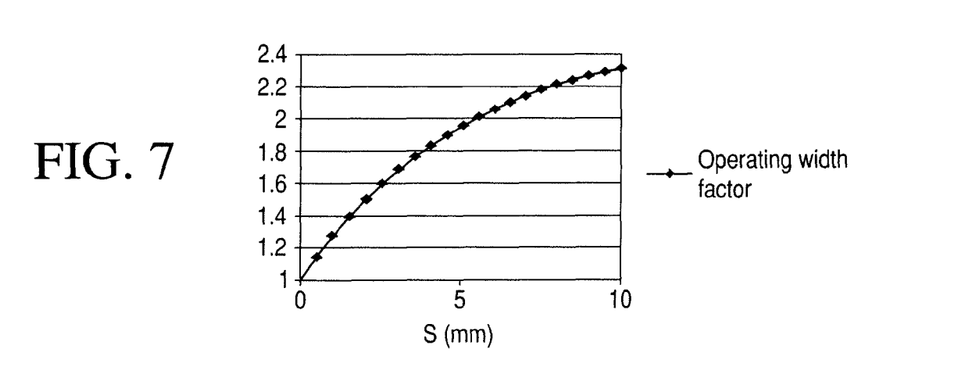
FIG. 7 is a graph representing an example of the relationship between the effective width of the receiver coils of FIG. 3 on the radial position of a detected particle.

The effective width WB depends on the radial position of the particle upon passage through the difference coil, its increasing with an increasing radial distance of the particle from the coil wall. This fact can be taken into account by the dependency of the effective width on the radial position of the particle being empirically determined at the factory for the respective type of particle counter. FIG. 7 shows an example for the relative increase of effective width with increasing radial particle distance s. Using this empirical curve, as is described more accurately below, the measured time difference $T_i$ can be corrected with respect to the radial distance of the particle i.

Figure 8:
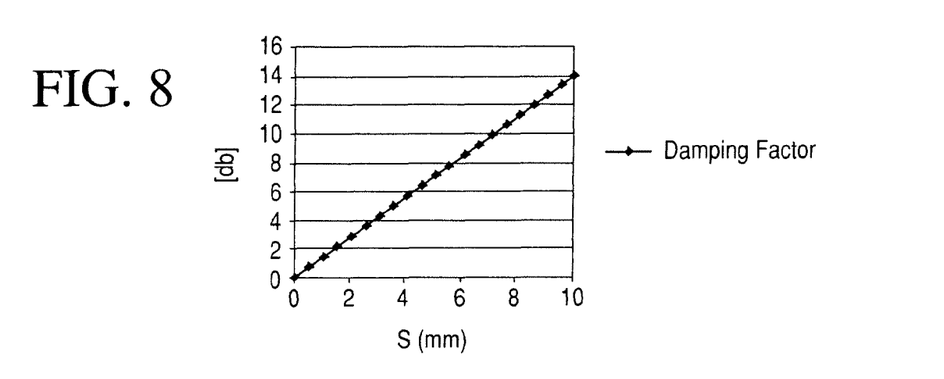
FIG. 8 is a graph representing an example of the relationship between attenuation of the signal of the receiver coils from FIG. 3 on the radial position of a detected particle.

Fundamentally, the maximum amplitude $A_i$ of the difference signal is a measure of the size of the particle i. However, in this connection, it must be considered that the attenuation of the difference coil depends on the radial position s of the particle, so that for a reliable estimation of the particle size the measured maximum amplitude $A_i$ must be corrected accordingly. This can take place by the dependency of the attenuation of the difference signal on the radial distance s from the coil wall being empirically determined at the factory for the respective type of particle counter. FIG. 8 shows one example for such a correction curve. The farther the particle radially from the coil system, the weaker the signal amplitude becomes. Here, the size of the particle also plays a certain part; the attenuation function with respect to distance, however, will run essentially the same.

Figure 6:
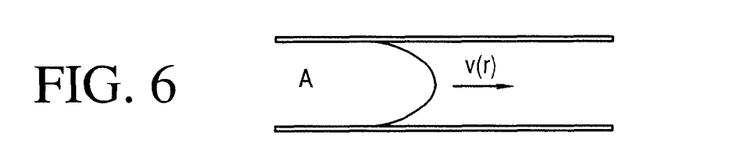
FIG. 6 is a graph of the theoretical radial velocity distribution in a laminar flow in a pipe.

Furthermore, with respect to the particle velocities, it must be considered that the velocity of a laminar flow in a pipe depends, in the known manner, on the radial distance r from the pipe wall, the dependency being parabolic and the maximum flow velocity being in the center of the pipe. Therefore, a certain distribution of the particle velocities, and thus, of the measured time differences $T_i$ is obtained for this reason.

In the evaluation of the difference signals, it is a good idea to make the following assumptions.

During a measurement interval of typically 1 to 30 minutes, the volumetric flow remains essentially constant, this of course also depending on the respective system. In practice, velocity fluctuations occur essentially when the system is started. During this time however no particle measurement takes place anyway. Otherwise, changes of the volumetric flow arise mainly due to fluctuations of the ambient temperature (effect on the viscosity of the lubricant) and due to the slowly changing permeability of the lubricant filter. Only in case of faults can rapid changes of the flow velocity occur, if, for example, a filter breaks.

2. The radial distance s of the particles to the coil system is uniformly distributed when viewed statistically.

3. Turbulent flow does not occur. This can be ensured by guide elements.

4. All particles are much smaller in their extension than the effective width of the coils.

One example for evaluation of difference signals is described below.

As already mentioned, during a measurement interval of typically 1 to 30 minutes, the maximum amplitude $A_i$ and the time difference $T_i$ for each detected particle i are stored. In order to enable reliable evaluation, a certain minimum number of particles should be determined. Optionally, for a small particle concentration, the measurement interval must be lengthened accordingly. As a result, a certain distribution of the maximum amplitudes and of the time differences is obtained. The smallest time differences $T_i$ represent particles in the center of the coil arrangement, i.e., $$s=r_0.$$

For the distribution of the flow velocity v(r) of a laminar flow in a pipe the following applies:

$$v(r) = \frac{\Delta p}{4 \cdot l \cdot \eta} \cdot (r_0^2 - r^2)$$

Here $\Delta p$ is the pressure difference in pascals, l is the length of the pipe in meters and q is the kinematic viscosity in Pa s.

The actual maximum velocity in the pipe can be estimated by the smallest measured time difference $T_i$ being divided by the factor "effective width" FW for $r_0$:

$$T'=\text{Min}(T_i)/FW(r_0).$$

Since we know the actual geometrical coil distance $d_{Sp}$ and now also the corrected time T', the maximum speed $v_{max}$ can be computed:

$$v_{max}=d_{sp}/T'.$$

For the mean velocity this yields $v_{mean}=v_{max}/2$. The following applies to the volumetric flow:

$$I=v_{mean}r_0^2\pi.$$

Since $v_{max}$ is known at this point, the constants $\Delta p/l \, \eta$ can be determined:

$$c = \frac{\Delta p}{l \cdot \eta} = \frac{4 \cdot v_{max}}{r_o^2}$$

Thus, the actual velocity distribution v(r) and v(s) in the pipe is now known. Therefore, the corrected time differences $T'_i(s)$ can be determined according to a computed effective width:

$$T'(s) = \frac{d_{Sp}}{v(s) \cdot FW(s)} = \frac{d_{Sp}}{\frac{c}{4}(r_o^2 - (r_o - s)^2) \cdot FW(s)}$$

Thus, for example, a table with values $T'_i(s)$ as a function of the radial distance s of the particle i to the coil is obtained. In the simplest case, this table can be used as a look-up table in order to assign a radial distance s to the coil to each found particle i. In this connection, the measured value $T_i$ is taken and the nearest value $T'_i(s)$ is sought in the table.

By means of this distance assignment, not only can the measured time difference, and thus, the computed particle velocity be corrected, but the measured maximum amplitude $A_i$ can also be corrected using the dependency of the difference signal attenuation on the radial particle distance s that has been empirically determined beforehand. Here, the amplitude value, in the simplest case, is reduced to a scalar, advantageously to the maximum value of the representation of the absolute value of the difference signal from FIG. 5. This value is then corrected with the appropriate attenuation value. Then, the value can be evaluated using the evaluation thresholds (for example, eight evaluation thresholds). Each evaluation range corresponds to a range of particle sizes. For each range, there is a counter which is incremented when the measured particle amplitude falls in this range. After the measurement interval, the total volume of the liquid is computed using the measurement duration and the determined volumetric flow and a contamination class is demonstrated according to the counts, for example, according to ISO 4406. Alternatively, the amplitude evaluation can take place based on a vector which has been assigned to the respective particle using the difference signal (in this connection not only the maximum amplitude value, but also the phase are considered).

It goes without saying that the empirically determined correction functions, as shown in FIGS. 7 & 8, can be represented by means of a balancing computation by suitable functions, for example, approximated parabolas and their inverse function. In this case, the look-up table can be omitted.

Immediately after turning on the particle counter, the flow velocity is still unknown, and thus, under certain circumstances, the particles cannot be reliably distinguished, since the assignment of the individual absolute-value signal arcs to the difference signal without knowledge of the expected range of the time differences $T_i$ to a certain event, specifically the passage of particle, is not always reliably possible. To circumvent this problem, as a "starting aid," a signal after exceeding the lower threshold value $S_u$ can be recorded in a length which is sufficient for recognizing a minimum flow velocity. The detected difference signals can then be separated using such a detected typical behavior or assigned to individual particle passages. This separation can take place, for example, by means of cross correlation with variation of the given effective widths or time differences $T_i$. In this connection, the given effective width or the given time difference is varied such that the amplitudes of the cross correlation function are maximized.

What is claimed is:

1. Process for detecting electrically conductive particles flowing in a liquid within a pipe section at a velocity v, comprising the steps of:
exposing the liquid to periodic alternating electromagnetic fields by means of a transmitter coil to induce eddy currents in the particles,
by means of a probe which is made as a coil arrangement and which is characterized by an effective width, producing a periodic electrical signal based on the eddy currents induced, the signal having a carrier oscillation with at least one of an amplitude and a phase which is modulated by the particles when the particles travel into the effective width of the coil arrangement,
filtering the signal by means of a frequency-selective first filter unit, sampling the signal filtered by the first filter unit by means of a triggerable A/D converter stage to obtain a demodulated digital measurement signal, filtering the digital measurement signal by means of a digital, frequency-selective adjustable second filter unit to obtain a useful signal, and evaluating the useful signal to detect passage of electrically conductive particles within the liquid moving in the pipe section, triggering A/D converter stage with a n-th, integral fraction of the frequency of the carrier oscillation, n being a function of a particle frequency which arises as the quotient of the flow velocity of the liquid v and the effective width of the coil arrangement, and setting the frequency-selective second filter unit as a function of the particle frequency, wherein the transmitter coil surrounds the pipe section, the coil arrangement having at least one first inductive receiver coil surrounding the pipe section and a second inductive receiver coil which is spaced axially relative to the first receiver coil and which surrounds the pipe section, the receiver coils being located in a region of the transmitter coil and are subtractively connected, the transmitter coil forming a primary side and the receiver coils forming a secondary side of a transformer arrangement, comprising the further steps of:

outputting a difference signal according to the eddy currents induced by the transmitter coil, forming the useful signal from the difference signal, estimating the flow velocity of the detected particles from the difference signal, and using the estimated flow velocity to determine the flow velocity v and using the flow velocity v to determine an operating state of a machine through which said liquid has passed.

2. Process in accordance with claim 1, wherein the pipe section is part of a lubricant circuit.

3. Process in accordance with claim 2, wherein the liquid is a lubricating oil of a machine.

4. Process in accordance with claim 1, wherein the transmission frequency of the transmitter coil is between 20 kHz and 500 kHz.

5. Process in accordance with claim 1, wherein the size of the detected particles is between 1 and 25 μm.

6. Process in accordance with claim 1, wherein the number of detected particles per unit of time is determined.

7. Process in accordance with claim 1, further comprising the step of determining the concentration of electrically conductive particles in the liquid.

8. Process in accordance with claim 1, wherein the transmitter coil is supplied with an alternating current voltage to produce periodic alternating electromagnetic fields, the alternating current voltage being produced from a binary signal by waveforming.

9. Process in accordance with claim 1, wherein the transmitter coil is induced by triggering with a PDM signal to emit a sinusoidal field.

10. Process in accordance with claim 8, wherein the trigger signal for the A/D converter stage is produced by the frequency of the binary signal used for producing the alternating current voltage for the transmitter coil being divided by n.

11. Process in accordance with claim 1, wherein n is chosen to be inversely proportional to the particle frequency for setting the trigger rate of the A/D converter stage to be at least roughly proportional to the particle frequency.

12. Process in accordance with claim 11, wherein n is chosen such that at least 5 samplings by the A/D converter stage fall within a time interval which corresponds to the inverse of the particle frequency.

13. Process in accordance with claim 11, wherein n is chosen such that at most 100 samplings by the A/D converter stage fall within a time interval which corresponds to the inverse of the particle frequency.

14. Process in accordance with claim 1, wherein the frequency-selective second filter unit is automatically set, depending on the particle frequency, by the second filter unit being clocked with a sampling rate of the A/D converter stage.

15. Process in accordance with claim 1, wherein the second filter unit has a low-pass filter to mask noise portions of the demodulated digital signal with frequencies above the particle frequency, a corner frequency of the low-pass filter being above the particle frequency.

16. Process in accordance with claim 1, wherein the second filter unit has a high-pass filter to add uniform portions of the demodulated digital signal, a corner frequency of the high-pass filter being below the particle frequency.

17. Process in accordance with claim 1, wherein the frequency of the carrier oscillation is chosen to be at least ten times the particle frequency.

18. Process in accordance with claim 1, wherein the A/D converter stage samples two values offset by a fixed phase difference when it is triggered to obtain the digital measurement signal as a two-component signal.

19. Process in accordance with claim 18, wherein the phase difference is 90° or m*360°±90°, m being a whole number.

20. Process in accordance with claim 18, wherein the two components of the digital measurement signal delivered by the A/D converter stage are filtered separately by means of the second filter unit to obtain the useful signal as a two-component signal.

21. Process in accordance with claim 20, wherein both components are considered in the evaluation of the useful signal.

22. Process in accordance with claim 1, wherein acting of the transmitter coil on the liquid with alternating electromagnetic fields is interrupted at least for part of each interval between two successive trigger signals for the A/D converter stage.

23. Process in accordance with claim 1, wherein the first filter unit has at least one low-pass filter which acts as an aliasing filter with respect to sampling by the A/D converter stage.

24. Process in accordance with claim 1, wherein the first filter unit has a high-pass filter to mask low frequency noise signals.

25. Process in accordance with claim 1, wherein the flow velocity v of the liquid is determined by measurement or is stipulated as a parameter.

26. Process in accordance with claim 1, wherein a controllable amplifier is connected upstream of the A/D converter stage to bring the signal to an amplitude which is optimally suited for the A/D converter stage.

27. Process in accordance with claim 1, wherein only difference signals which have an amplitude which exceeds a certain threshold value are used for particle detection.

28. Process in accordance with claim 27, wherein the difference signal is recorded as long as the signal amplitude exceeds the threshold value.

29. Process in accordance with claim 1, wherein a radial distance of the detected particles from the receiver coil wall is estimated from the difference signal.

30. Process in accordance with claim 1, wherein the flow velocity of the detected particles is estimated from the time interval of the maximum and minimum values of the difference signal.

31. Process in accordance with claim 1, wherein the flow velocity of the detected particles is estimated from the time interval of peaks of the absolute value of the difference signal.

32. Process in accordance with claim 30, wherein the distribution of the determined time intervals is determined and subjected to statistical analysis.

33. Process in accordance with claim 32, wherein the theoretical radial distribution of the flow velocity in a laminar flow is considered in the statistical analysis of the determined time intervals.

34. Process in accordance with claim 33, wherein the flow velocity of the liquid v is determined from a peak of the estimated particle velocities with consideration of the geometrical distance of the receiver coils.

35. Process in accordance with claim 29, wherein the estimated radial distance of the detected particles from the receiver coil wall is used in the estimation of the flow velocity of the particles.

36. Process in accordance with claim 35, wherein the dependency of the effective width of the receiver coils on the radial distance of the detected particle from the receiver coil wall is empirically determined beforehand.

37. Process in accordance with claim 36, wherein the theoretical radial distribution of the flow velocity in a laminar flow, the geometrical distance of the receiver coils and the dependency of the effective width of the receiver coils on the radial distance of the particles determined beforehand are considered in the estimation of the radial distance of the detected particles from the receiver coil wall.

38. Process in accordance with claim 1, wherein the size of the detected particles is estimated from the difference signal and the detected particles are classified according to the estimated size.

39. Process in accordance with claim 38, wherein the difference signal is recorded as long as the signal amplitude exceeds the threshold value, and wherein the estimated radial distance of each detected particle from the receiver coil wall is used in the estimation of the particle size.

40. Process in accordance with claim 39, wherein the dependency of the amplitude of the difference signal on the radial distance of the particle from the receiver coil wall is empirically determined beforehand.

41. Process in accordance with claim 40, wherein the theoretical radial distribution of the flow velocity in a laminar flow, the geometrical distance of the receiver coils, the dependency of the effective width of the receiver coils on the radial distance of the particles from the receiver coil wall determined beforehand, and the dependency of the amplitude of the difference signal on the radial distance of the particles from the receiver coil wall determined beforehand are considered in the estimation of size the of the detected particles.

42. Process in accordance with claim 1, wherein the probe signal, before it is supplied to the triggerable A/D converter stage, is subjected to an offset voltage to compensate for a coil offset voltage.

43. Process in accordance with claim 42, wherein the offset voltage is generated by means of a D/A converter, the value of the offset voltage resulting from the averaging of the demodulated digital measurement signal.

44. Process in accordance with claim 43, wherein averaging takes place while the probe signal is being subjected to the offset voltage.

45. Process in accordance with claim 43, wherein averaging takes place before the probe signal is subjected to the offset voltage.

46. Device for detecting electrically conductive particles in a liquid flowing within a pipe section with a velocity v, comprising:
a transmitter coil which surrounds the pipe section for exposing the liquid to periodic alternating electromagnetic fields to induce eddy currents in the particles,
a probe having a coil arrangement having at least one first inductive receiver coil surrounding the pipe section and a second inductive receiver coil which is spaced axially relative to the first receiver coil by an effective width for producing a periodic electrical signal based on the eddy currents induced, the signal produced having a carrier oscillation with at least one of an amplitude and phase which is modulated by the particles when the particles travel across the effective width of the coil arrangements, the receiver coils being located in a region of the transmitter coil and being subtractively connected so as to output a difference signal according to the eddy currents induced by the transmitter coil,
a frequency-selective first filter unit for filtering said signal,
a triggerable A/D converter stage for sampling the signal which has been filtered by the first filter unit to obtain a demodulated digital measurement signal,
a trigger means for triggering the A/D converter stage with a n-th integral fraction of the frequency of the carrier oscillation, n being a function of the particle frequency which arises as the quotient of the flow velocity of the liquid and the effective width of the probe,
a digital frequency-selective second filter unit which can be adjusted depending on the particle frequency for filtering the digital measurement signal for purposes of obtaining a useful signal from the difference signal, and
an evaluation unit for evaluating the useful signal for purposes of detecting the passage of electrically conductive particles in the pipe section, the evaluation unit being adapted for estimating the flow velocity of the detected particles from the difference signal, for using the estimated flow velocity to determine the flow velocity v and for determining an operating state of a machine through which said liquid has passed based at least in part upon the flow velocity v.

47. Device in accordance with claim 46, wherein the transmitter wherein the transmitter coil forms a primary side and the receiver coils form a secondary side of a transformer arrangement.

48. Device in accordance with claim 47, wherein the diameter of each receiver coil is smaller than the diameter of the transmitter coil.

49. Device in accordance with claim 47, wherein all receiver coils are located entirely within the transmitter coil.

50. Device in accordance with claim 49, wherein the extension of the transmitter coil in the axial direction is at least twice as great as the axial extension of the arrangement of the receiver coils.

51. Device in accordance with claim 47, wherein there are exactly two of the receiver coils.

52. Device in accordance with claim 46, wherein there are a binary signal source and a waveformer to produce a supply voltage signal for the transmitter from a binary signal by means of waveforming.

53. Device in accordance with claim 52, wherein the trigger means has a divider to produce the trigger signal for the A/D converter stage from the binary signal for the waveformer by means of dividing by n.

54. Device in accordance with claim 53, wherein the binary signal source is a timer.

55. Device in accordance with claim 46, wherein the A/D converter stage has a resolution of at least 16 bits.

56. Device in accordance with claim 46, wherein the A/D converter stage has at least one flash converter or SAR converter.

57. Device in accordance with claim 55, wherein the second filter unit is formed by a digital signal processor.

58. Device in accordance with claim 55, wherein the A/D converter stage has two A/D converters which are connected in parallel, the two A/D converters being triggered with the same frequency so that they sample offset by a fixed phase difference to obtain the digital measurement signal as a two-component signal.

* * * * *